United States Patent [19]
Ring et al.

[11] 3,964,488
[45] June 22, 1976

[54] TRACHEAL TUBE

[75] Inventors: Wallace H. Ring; John C. Adair; Richard A. Elwyn, all of Salt Lake City, Utah

[73] Assignee: Wallace H. Ring, Salt Lake City, Utah

[22] Filed: Nov. 13, 1974

[21] Appl. No.: 523,250

[52] U.S. Cl. .............................................. 128/351
[51] Int. Cl.² ....................................... A61M 16/00
[58] Field of Search .................................... 128/351

[56] References Cited
UNITED STATES PATENTS

| | | | |
|---|---|---|---|
| 3,599,642 | 8/1971 | Tindel | 128/351 |
| 3,606,669 | 9/1971 | Kemble | 128/351 X |
| 3,788,326 | 1/1974 | Jacobs | 128/351 X |
| 3,848,605 | 11/1974 | Harautuneian et al. | 128/351 |

*Primary Examiner*—Channing L. Pace
*Attorney, Agent, or Firm*—Mallinckrodt & Mallinckrodt

[57] ABSTRACT

A tracheal tube that may be constructed for either oral or nasal use is preformed as a flexible integral unit from flexible material having a memory so as to return to preformed shape following flexure. The tube has a proximal or machine end portion and a distal or patient end portion interconnected along the length of the tube by an intermediate portion and an abrupt bend portion. The distal or patient end portion and the adjoining intermediate portion merge into each other along the length of the tube and include curvature such that they will positionally conform to the shape of a patient's posterior pharynx and trachea and extend therealong when the tracheal tube is installed for use. The abrupt bend portion interconnects the proximal or machine end portion and the intermediate portion along the length of the tube at an angle substantially no greater than 90°, so such proximal or machine end portion will be located exteriorly of the body opening of the patient and will extend along the face of the patient exteriorly of such body opening when the tracheal tube is installed for use. In those embodiments intended for oral use, the distal or patient end portion extends in the same general direction as the proximal or machine end portion. In those intended for nasal use, the distal or patient end portion extends in the opposite direction. In both instances, there is a springlike action from the bend portion toward the distal or patient end of the tube that tends to hold the tube in place without harming delicate tissues. A pair of ports are preferably provided adjacent the distal or patient end of the tube as a safety measure to supply ventilation to both the right and th left lungs during anesthesia should the tube be accidentally advanced beyond the trachea.

10 Claims, 17 Drawing Figures

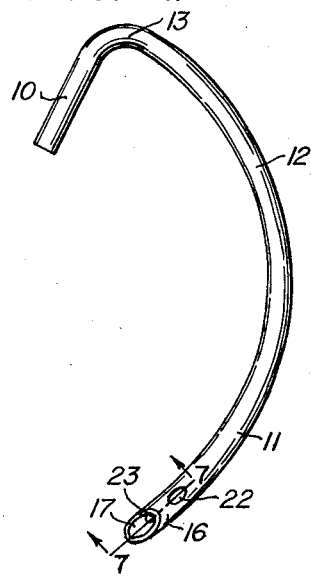
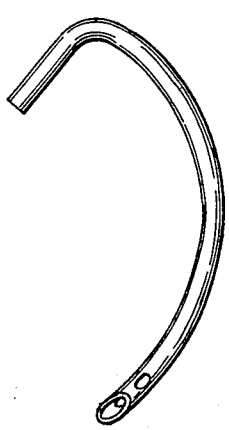
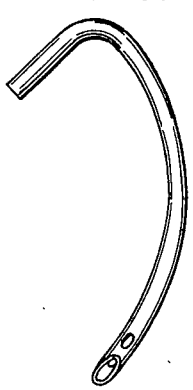
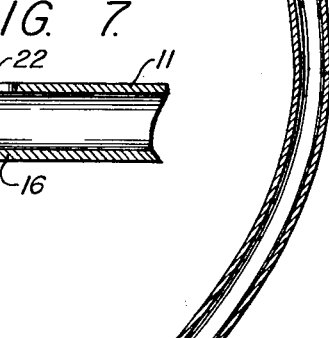
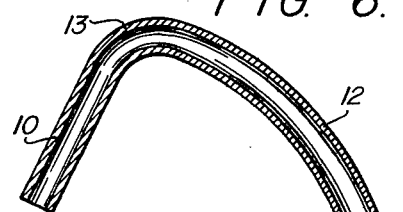
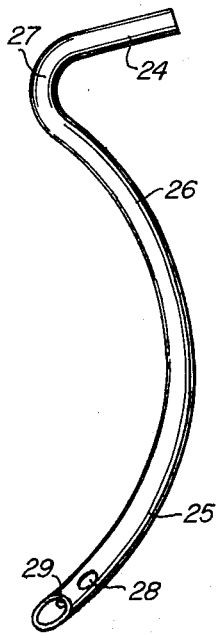
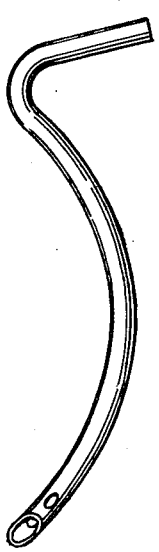
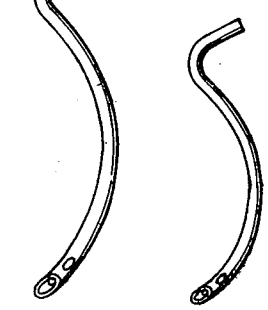

FIG. 17.

| AGE | SIZE I.D. (mm) | SIZE R.A.E. O.D. Fr. (mm) | | R.A.E. Oral | R.A.E. Nasal | McIntyre (9) (Oral) | Collins (10) (Length, incisors to cords) | Smith (11) (Oral 20% longer for Nasal) | ANSI-Oral (12) Min. Length | ANSI-Oral (12) Pre-Cut Length |
|---|---|---|---|---|---|---|---|---|---|---|
| Newborn | 3.0 | 4.2 | 13 | 10.5 | 11.5 | | | | | |
| 4 weeks 6 months | 3.5 | 4.8 | 15 | 12 | 14 | | | | 16 | 11 |
| 6 months 1 year | 4.0 | 5.5 | 17 | 13 | 15.5 | | 8 | 10-13 | 18 | 12 |
| 1 year 2 years | 4.5 | 6.1 | 19 | 15 | 18 | | | 14 | 20 | 13 |
| 3 years | | | | | | | 9 | | 22 | 14 |
| 2-4 years | 5.0 | 6.8 | 21 | 16.5 | 19 | 13.25 | | 16 | | |
| 4 years | | | | | | 13.75 | 9.5 | | 24 | 15 |
| 4-5½ years | 5.5 | 7.4 | 23 | | 19.5 | | | 16 | | |
| 6 years | | | | | | 14.25 | 10 | | 27 | 16 |
| 5-7 years | | | | | | | | 17 | | |
| 7 years | | | | | | 14.50 | 10.5 | | | |
| 5½ years 7½ years | 6.0 | 8.1 | 25 | 17.5 | 20.5 | | | | | |
| 8 years | | | | | | 15.25 | 11 | 18 | 28 | 18 |

TRACHEAL TUBE

BACKGROUND OF THE INVENTION

1. Field

The invention is in a specialized field of equipment for medical use, specifically tracheal tubes as used for conducting gases or vapors along the trachea, as for example by anesthesiologists in the administration of anesthesia to patients undergoing surgery.

2. State of the Art

Since the first reported use of a straight tracheal tube for the administration of anesthesia in the year 1889, such tubes have been designed with various shapes and curvatures and have been made either rigid or flexible. Flexible tubes automatically conform in shape and curvature to body requirements in individual instances, but have proven dangerous in that kinking has occurred and has resulted in critical stoppages in flow. A non-kinking, preformed, flexible tube of L-shape, a so-called "Oxford Tube", having a widely curved, right-angle bend adapted for placement in the trachea and posterior pharynx, is known, and a similar tube having a sigmoid curvature for similar placement in the trachea and posterior pharynx is proposed by Kuhn in his U.S. Pat. No. 3,363,629. Neither of these tracheal tubes are entirely satisfactory. In most tracheal tubes presently used, a port — a so-called "Murphy eye" — is provided in one side of the distal end portion of the tube as a safety measure against accidental advancement of the tube onto the carina at the lower end of the trachea.

SUMMARY OF THE INVENTION

In order to eliminate any chance of kinking, the tracheal tube of the present invention is provided (as is the Oxford tube) with a preformed abrupt bend portion. However, in contrast to the Oxford tube, the placement of such bend portion is between a relatively short, rectilinear, proximal or machine end portion that is adapted to extend along the face, exteriorly of the body, and a closely adjoining, intermediate portion that merges smoothly and integrally into a distal or patient end portion, the latter two portions including curvature such that they will positionally conform to the shape of a patient's posterior pharynx and trachea and extend therealong when the tracheal tube is installed for use. Such latter portions have a spring-like action that tends to hold the tube in place during use while exerting only a gentle and non-traumatic pressure against tender body tissues. The preformed abrupt bend portion is at the location of emergence of the device from the body.

Preshaped in this manner, the device of the invention has the advantage of eliminating the possibility of kinking at the bend location and of placing all adaptors and utility connections away from the body opening into which the tracheal tube extends. This not only provides better access for the surgeon during head and neck surgery, but also prevents injury to the patient from pressure by the relatively heavy adaptors and connectors in common use.

Embodiments of the invention intended for oral use have the proximal or machine end extending in the same general direction as the distal or patient end, while in those intended for nasal use the reverse holds true.

The lengths of the endotracheal tubes of the invention will vary in accordance with different sizes of individual patients, though careful research has determined a range of lengths accommodating practically anyone. Despite the selection of a proper length for any given patient, there is always the danger that slippage could advance the outlet end of the tube into the right main stem bronchus and thereby effectively cut off flow into the left lung. To avoid this danger, the usual Murphy eye on the long side of the tube adjacent the usual beveled outlet end is supplemented by a second eye or port on the opposite short side of the tube adjacent the beveled outlet end and opposite the Murphy eye. This supplemental eye or port insures ventilation of the left lung as well as the right upper lobe.

THE DRAWINGS

Embodiments representing the best mode presently contemplated of carrying out the invention in actual practice are illustrated in the accompanying drawings in which:

FIGS. 1, 2, 3, 4, and 5 are corresponding side elevational views of endotracheal tubes of the invention constructed for oral use and exemplifying different sizes for the tubes;

FIG. 6, an axial section along the length of the tube of FIG. 1 extending from end to end thereof, the view being drawn to a larger scale;

FIG. 7, a fragmentary longitudinal section taken along the line 7—7 of FIG. 1 and drawn to a larger scale than FIG. 6;

FIG. 8, a view in side elevation of a patient undergoing anesthesia by means of the oral endotracheal tube of FIG. 2, the location of the tube relative to the posterior pharynx and trachea being indicated by dotted lines;

FIGS. 9, 10, 11, 12, and 13, views corresponding to those of FIGS. 1–5, but illustrating different sizes of endotracheal tubes of the invention constructed for nasal use;

FIG. 14, a view corresponding to that of FIG. 8, but with respect to a patient undergoing anesthesia by means of the nasal tube of FIG. 10;

FIG. 15, a view in side elevation of an oral endotracheal tube of the invention of Oxford Tube style;

FIG. 16, a corresponding view of a similar nasal endotracheal tube; and

FIG. 17, a table of optimum tube sizes and lengths for different age groups as determined experimentally.

DETAILED DESCRIPTION OF THE ILLUSTRATED EMBODIMENTS

Figure 15:
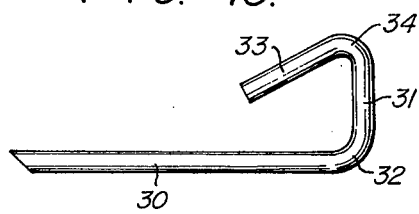

As illustrated in FIGS. 1–5, wherein like parts are indicated by the same reference numbers, oral endotracheal tubes of the invention each comprise a proximal or machine end portion 10 and a distal or patient end portion 11 interconnected along the length of the tube by an intermediate portion 12 and by an abrupt bend portion 13. As can be seen, the distal or patient end portion 11 and the adjoining intermediate portion 12 smoothly merge into each other along the length of the tube and include curvature such that they will positionally conform to the shape of a patient's posterior pharynx and trachea, indicated generally at 14 and 15, respectively, in FIG. 8. The distal or patient end portion terminates in a beveled terminal end 16 for the tube that provides an outlet orifice 17. The intermediate portion 12 smoothly merges into abrupt bend portion 13, which, in turn, smoothly merges into proximal or machine end portion 10.

Figure 8:
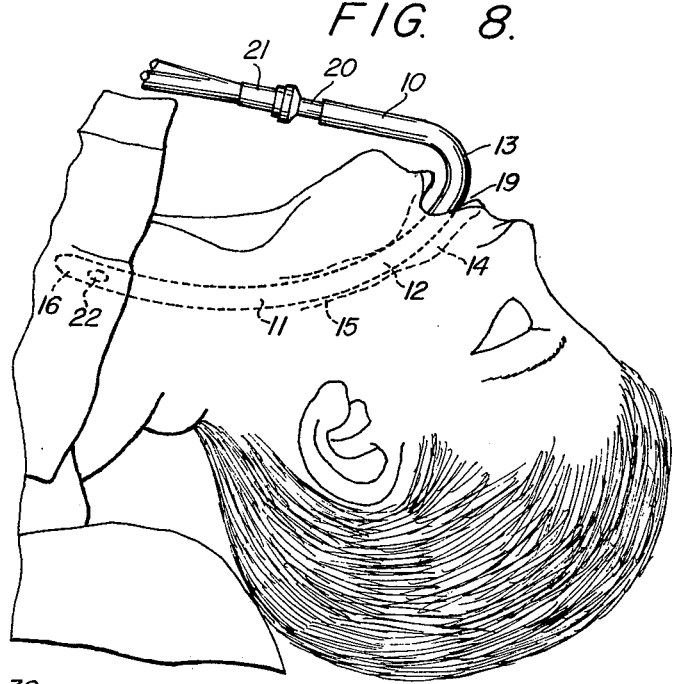

The proximal or machine end portion 10 advantageously extends rectilinearly from abrupt bend portion 13, so as to extend downwardly along the lower lip and chin of a patient when installed, for example, for purposes of administering anesthesia, see FIG. 8. It could extend otherwise, however, e.g. slightly curved and askew from the rest of the tube. The intermediate portion 12 and distal or patient end portion 11 are preferably both curved along their lengths and extend in the same general direction as the proximal end portion 10. The abrupt bend portion 13 is preferably somewhat less than 90° measured between an extension of the proximal or machine end portion and an intersecting tangential extension of the intermediate portion, so as to be acute in character and position the proximal or machine end portion 10 exteriorly of the mouth 19 of the patient when installed as in FIG. 8. The usual adapter 20 and utility connection 21 are therefore positioned away from the body opening, here the mouth 19, into which the tracheal tube extends.

The degree of curvature included by the distal or patient end portion 11 and by the intermediate portion 12 will depend upon the size of the device, as can be seen from the five different sizes shown. As shown, the curvature of the former smoothly continues the curvature of the latter although not necessarily nor usuallly on the same radius, it being realized that the entire curvature sought is one that largely conforms to the posterior pharynx and trachea of a human being.

The endotracheal tube as heretofore described is preferably integrally preformed from a suitable flexible thermoplastic material, such as polyvinylchloride, polyethelyne, or the like, having a memory, i.e. having sufficient resiliency to return to position following flexure. Thus, although the tube has reasonable flexibility, enabling it to conform to environment rather than compelling the environment to conform to it, bend portion 13 essentially retains its configuration and is not subject to the danger of kinking during use, such as in the administration of a anesthetic.

A feature of the invention is the provision of a supplemental eye or port 22, FIG. 7, adjacent to the beveled terminal end 16 of the distal or patient end portion 11 and on the short wall side of such beveled terminal end, additional to the usual Murphy eye or port 23 on the long wall side of such beveled terminal end 16. This is a safety feature, in that it provides ventilation for the left lung as well as for the right upper lobe should the tube be accidentally advanced onto the carina at the lower end of the trachea or into the right main stem bronchus.

Figure 14:
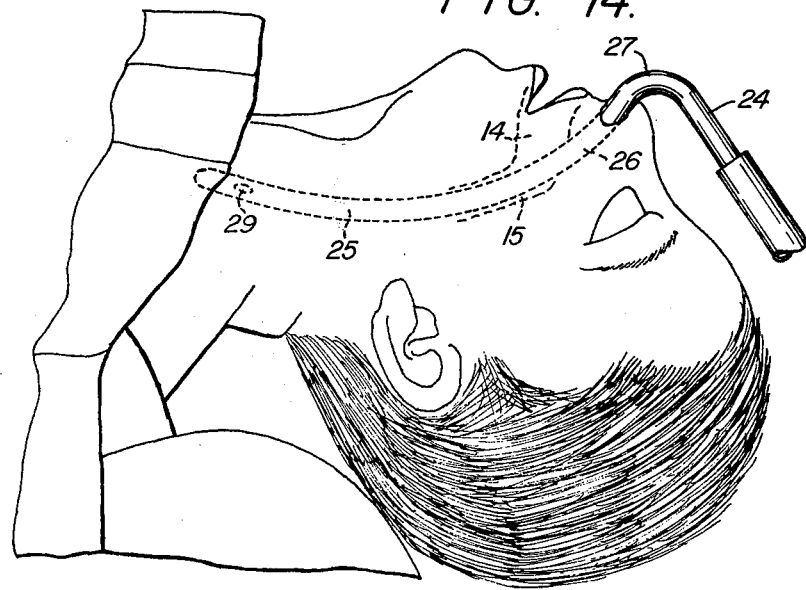

The endotracheal tubes of FIGS. 9–13 are constructed for nasal use in the manner indicated in FIG. 14. They are similar to the oral endotracheal tubes of FIGS. 1–5 so far as their component parts are concerned. Thus, each has a proximal or machine end portion 24, a distal or patient end portion 25, an intermediate portion 26 and an abrupt bend portion 27, all arranged similarly to the corresponding components of the oral endotracheal tubes of FIGS. 1–5, except that the bend portion 27 and proximal or machine end portion 24 are reversed in position as illustrated. Each is advantageously provided with an eye or port 28 supplemental to the usual Murphy eye 29 as in the previously described oral endotracheal tubes of FIGS. 1–5.

In contrast to non-preformed flexible endotracheal tubes commonly used at the present time, wherein excessive tube length is supplied at the upper or proximal end for cutting off by the anesthesiologist to fit individual patients the devices of the present invention are preferably provided in ranges of sizes such as are shown in FIG. 1–5 and FIGS. 9–13. Optimum lengths have been arrived at by careful research, using chest radiograms, and are given in the table of FIG. 17 for a complete range of ages using optimum tube sizes.

Although the foregoing embodiments of the invention represent the best mode presently contemplated for carrying out the invention, it is possible to incorporate the inventive concepts in both oral and nasal endotracheal tubes of Oxford Tube type, wherein the distal or patient end portion of the tube is rectilinear and connects with an adjoining rectilinear portion (which, in the usual Oxford Tube, is the proximal or machine end portion) by means of a right-angle bend, such distal or patient end portion, such adjoining rectilinear portion, and such right-angle bend fitting into and more or less conforming to the posterior pharynx and trachea of a patient.

Thus, as illustrated in FIG. 15, which shows an oral endotracheal tube of that type in accordance with the present invention, a distal or patient end portion 30 of rectilinear formation connects with an adjoining intermediate portion 31, also of rectilinear formation, through a right-angle bend 32, and such intermediate portion 31 is connected with a proximal or machine end portion 33 by means of an abrupt bend portion 34. It can be seen that right-angle bend 32 provides the curvature which is included by the distal or patient end portion and by the intermediate portion and which enables such portions to fit into and more or less conform to the shape of a patients posterior pharynx and trachea, but the proximal or machine end portion is exterior of the body cavity. Accordingly, even though this embodiment of the invention is of Oxford Tube type, it does have the basic advantages and characteristics of the present invention.

Figure 16:
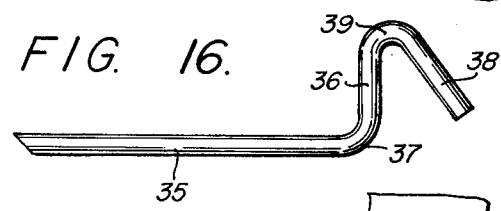

The same can be said of the Oxford Tube type of nasal endotracheal tube of the invention illustrated in FIG. 16. There, rectilinear distal or patient end portion 35 connects with rectilinear intermediate portion 36 through a right-angle bend 37, and such intermediate portion 36 connects with proximal or machine end portion 38 by means of an abrupt bend portion 39.

Although it is preferred to fabricate the device of the invention from suitable plastic materials of the type previously indicated having the required flexibility within the limits of the preformed formation, the device being thereby a wholly integral unit, it is possible to obtain the required "memory" for the preformed shape by incorporating into a pliable non-preformed tube of suitable plastic or other material, one or more spring components imparting the required shape and memory, and non-kinking characteristics to the non-preformed pliable tube.

It should be realized that the novel feature explained above of providing double Murphy's eyes adjacent the beveled terminal end of the distal or patient end portion of a tracheal tube is of general application in the tracheal tube art.

From the drawings, it can be seen that in all embodiments of the invention the proximal or machine end portion of the trachea tube terminates in a free end adapted for attachment to a machine with which the tracheal tube is to be used, that the entire tube is of substantially uniform diameter externally and internally prior to attachment to a machine connector, and that the proximal or machine end portion is sufficiently long in any given size of tracheal tube to position the bend portion at the location of emergence of the tube from the patient's body opening through which the tracheal tube extends and the machine connector well away from such body opening. This means, considering the total combination as previously described, that the adaptor or other cumbersome connector commonly employed with machines of this type is located well away from the body cavity of the patient during use, which is a very important feature of the invention.

Whereas this invention is here illustrated and described with respect to embodiments presently contemplated as the best mode of carrying out the invention in actual practice, as well as with respect to less desirable embodiments, it should be understood that various changes may be made within the teachings hereof without departing from the generic scope of the invention as pointed out in the following claims.

What we claim is:

1. A preformed, flexible, elongate, tracheal tube made of flexible material having a memory so said tube will return to its preformed shape following flexure, comprising a proximal or machine end portion of the length of the tube having its terminal end open and adapted for connection with a source of gas to be introduced into the lungs of a patient; a distal or patient end portion of the length of the tube having its terminal end portion open and beveled; an intermediate portion of the length of the tube; and a preformed abrupt bend portion of the length of the tube; said distal or patient end portion and said intermediate portion merging into each other along the length of the tube and including curvature such they will positionally conform approximately to the shape of a patient's posterior pharynx and trachea and extend therealong when said tracheal tube is installed for use, and said bend portion interconnecting said proximal or machine end portion and said intermediate portion along the length of the tube at an angle substantially no greater than 90° so said proximal or machine end portion will be located exteriorly of the body opening of the patient and will extend along the face of the patient exteriorly of said body opening when said tracheal tube is installed for use, said proximal or machine end portion terminating in a free end adapted for attachment to a machine with which the tracheal tube is to be used, the entire tube being of substantially uniform diameter externally and internally prior to attachment to a machine connector, and said proximal or machine end being sufficiently long in any given size of tracheal tube to position the bend portion at the location of emergence of the tube from a patient's body opening through which the tracheal tube extends and the machine connector well away from said body opening.

2. A tracheal tube in accordance with claim 1, wherein the flexible material is a thermoplastic material preformed to the shape described.

3. A tracheal tube in accordance with claim 1, wherein the abrupt bend portion interconnects the proximal or machine end portion and the intermediate end portion along the length of the tube at an acute angle.

4. A tracheal tube in accordance with claim 1, wherein the curvature included by the distal or patient end portion and by the intermediate portion constitutes arcuate formation of both said distal or patient end portion and said intermediate portion.

5. A tracheal tube in accordance with claim 4, wherein the proximal or machine end portion is rectilinear in formation.

6. A tracheal tube in accordance with claim 1, wherein the proximal or machine end portion extends in approximately the same direction as does the distal or patient end and thereby adapts the tracheal tube for oral use.

7. A tracheal tube in accordance with claim 1, wherein the proximal or machine end portion extends in approximately the opposite direction as does the distal or patient end portion and thereby adapts the tracheal tube for nasal use.

8. A tracheal tube in accordance with claim 1, wherein the distal or patient end portion is of substantially rectilinear formation, the intermediate portion is also of substantially rectilinear formation, and the curvature included by said portions is a substantially 90° bend connection between the said portions.

9. A tracheal tube in accordance with claim 1, wherein the distal or patient end portion has a beveled terminal end resulting in a long wall side for the tube and in an opposite short wall side, a Murphy's eye is provided adjacent said beveled terminal end on the long wall side thereof, and a second Murphy's eye is provided adjacent the said beveled terminal end on the short wall side thereof and directly opposite the first Murphy's eye, the tube being otherwise imperforate.

10. In a tracheal tube having a distal or patient end portion which has a beveled terminal end resulting in a long wall for the tube and in an opposite short wall side for the tube, and has a Murphy's eye adjacent the said beveled terminal end on the long wall side of the tube and a second Murphy's eye adjacent said beveled terminal end on the short wall side of the tube directly opposite the first Murphy's eye, the tube being otherwise imperforate.

* * * * *

UNITED STATES PATENT OFFICE
CERTIFICATE OF CORRECTION

PATENT NO. : 3,964,488
DATED : June 22, 1976
INVENTOR(S) : Wallace H. Ring; John C. Adair; Richard A. Elwyn It is certified that error appears in the above-identified patent and that said Letters Patent are hereby corrected as shown below:

Abstract, line 28, change "th" to --the--.

Column 4, line 64, change "trachea" to --tracheal--.

Column 6, line 47, after "long wall" insert --side--.

Signed and Sealed this

Fourth Day of January 1977

[SEAL]

Attest:

RUTH C. MASON
Attesting Officer

C. MARSHALL DANN
Commissioner of Patents and Trademarks